(12) United States Patent
Goepferich et al.

(10) Patent No.: US 9,579,394 B2
(45) Date of Patent: Feb. 28, 2017

(54) POLYANION NANOCOMPLEXES FOR THERAPEUTIC APPLICATIONS

(75) Inventors: Achim Goepferich, Sinzing (DE); Matthias Ferstl, Parsberg (DE)

(73) Assignee: UNIVERSITAET REGENSBURG, Regensburg (DE)

( * ) Notice: Subject to any disclaimer, the term of this patent is extended or adjusted under 35 U.S.C. 154(b) by 0 days.

(21) Appl. No.: 14/237,445

(22) PCT Filed: Aug. 7, 2012

(86) PCT No.: PCT/EP2012/065470
§ 371 (c)(1),
(2), (4) Date: Feb. 21, 2014

(87) PCT Pub. No.: WO2013/020986
PCT Pub. Date: Feb. 14, 2013

(65) Prior Publication Data
US 2014/0171368 A1 Jun. 19, 2014

(30) Foreign Application Priority Data

Aug. 8, 2011 (DE) .................. 10 2011 109 683
Feb. 1, 2012 (DE) .................. 10 2012 001 844

(51) Int. Cl.
*A61K 47/48* (2006.01)
*C12N 15/88* (2006.01)

(52) U.S. Cl.
CPC ... *A61K 47/48246* (2013.01); *A61K 47/48323* (2013.01); *C12N 15/88* (2013.01)

(58) Field of Classification Search
CPC .............................................. A61K 47/48246
See application file for complete search history.

(56) References Cited

U.S. PATENT DOCUMENTS

| 2006/0193825 A1 | 8/2006 | Musso et al. |
| 2007/0185033 A1 | 8/2007 | Gefter et al. |
| 2010/0129460 A1* | 5/2010 | Adami et al. ............... 424/499 |
| 2010/0311821 A1 | 12/2010 | Geng |

FOREIGN PATENT DOCUMENTS

WO 2011/109698 A1 9/2011

OTHER PUBLICATIONS

Dong-Wook Ryu et al., "Amphiphilic peptides with arginines and valines for the delivery of plasmid DNA", Journal of Cellular Biochemistry, vol. 112, No. 5, May 1, 2011, pp. 1458-1466. XP055045696.
Tu Raymond S. et al., "Cooperative DNA binding and assembly by a bZip peptide-amphiphile", Soft Matter, vol. 6, No. 5, Jan. 11, 2010, pp. 1035-1044. XP055045728.
Ferstl M. et al., "Characterization of Nanostructured Poly-Electrolyte Peptide Complexes", Posterbeitraege Pharmazeutische Technologie, Abstract T012, Duetsche Pharmazeutische Gesellschaft-Jahrestragung 2010, Oct. 4-7, 2010, XP002688155.
Ferstl M. et al., "Nanofibers Resulting from Cooperative Electrostatic and Hydrophobic Interactions between Peptides and Polyelectrolytes of Opposite Charge", Langmuir, vol. 27, No. 23, Dec. 6, 2011, pp. 14450-14459, XP055045725.
A. Graff, D. Tropel, SK. Raman, G. Machaidze, A. Lustig and P. Burkhard, "Peptidic nanoparticles for cancer therapy and diagnosis", NSTI-Nanotech 2005, vol. 1, 2005, 112-115.
K. Bowman and K. W. Leong, "Chitosan nanopartilces for oral drug and gene delivery", Int. J. Nanomedicine 2006:1(2) 117-128.

* cited by examiner

*Primary Examiner* — Amber D Steele
(74) *Attorney, Agent, or Firm* — Mayer & Williams PC; Ann Wieczorek (57) ABSTRACT

The subject-matter of the present invention are nanocomplexes of polyanions and cationic peptides which are, e.g., suitable for the transport of drugs into cells and their controlled release in the organism, as well as a complex material in which the nanocomplexes are bonded to a biologically active unit for the selective recognition of tissues, cells or organelles.

6 Claims, 4 Drawing Sheets

SEQUENCE LISTING

<160> NUMBER OF SEQ ID NOS: 4

<210> SEQ ID NO 1
<211> LENGTH: 21
<212> TYPE: RNA
<213> ORGANISM: Artificial sequence
<220> FEATURE:
<223> OTHER INFORMATION: /note="Description of artificial sequence:
      DS1-siRNA"

<400> SEQUENCE: 1
gcaagcugac ccugaaguuc a                                              21

<210> SEQ ID NO 2
<211> LENGTH: 21
<212> TYPE: RNA
<213> ORGANISM: Artificial sequence
<220> FEATURE:
<223> OTHER INFORMATION: /note="Description of artificial sequence:
      DS2-siRNA"

<400> SEQUENCE: 2
gaacuucagg gucagcuugc c                                              21

<210> SEQ ID NO 3
<211> LENGTH: 21
<212> TYPE: DNA
<213> ORGANISM: Artificial sequence
<220> FEATURE:
<223> OTHER INFORMATION: /note="Description of artificial sequence:
      DS1-DNA"

<400> SEQUENCE: 3
atgaacttca gggtcagttg c                                              21

<210> SEQ ID NO 4
<211> LENGTH: 22
<212> TYPE: DNA
<213> ORGANISM: Artificial sequence
<220> FEATURE:
<223> OTHER INFORMATION: /note="Description of artificial sequence:
      DS2-DNA"

<400> SEQUENCE: 4
tacttgaagt cccagtcgaa cg                                             22

POLYANION NANOCOMPLEXES FOR THERAPEUTIC APPLICATIONS

This application is a 35 U.S.C. 371 submission of PCT Patent application serial number PCT/EP2012/065470 filed Aug. 7, 2012 entitled "POLYANION NANOCOMPLEXES FOR THERAPEUTIC APPLICATIONS", which is hereby incorporated by reference in its entirety.

The subject-matter of the present invention are nanocomplexes of polyanions and peptides which are, e.g., suitable for the transport of drugs into cells and their controlled release in the organism. Certain structural properties of a peptide enable the latter to undergo cooperative electrostatic and hydrophobic interactions with polyanions. On a molecular level, this results in the formation of nanocomplexes which are preferably linear. A characteristic of the complexes is that per negative charge of the polyanion, a positive charge of a peptide is available to form the complex. In this context, e.g., by the use of nucleic acid sequences comprising only a few base pairs as the polyanion, nanocomplexes having a size of less than 10 nm can be prepared. This means a considerable reduction in size, e.g., as compared with polyplexes of polycations and polyanions in which random arrangement of polyanions and polycations takes place. One great advantage of the complexes is that due to the small size, their incorporation into cells can be realized. This can be enhanced by attachment of suitable biologically active molecules which interact with specific surface structures of cells. Moreover, it is possible to attach spacers, such as, e.g., PEG chains, to the peptides to increase the circulation half-life of the complexes in the blood or to anchor the biologically active molecules to the complex.

The transport of nucleic acids, proteins and peptides into tissue and cells is of outstanding importance for the therapy of numerous diseases of the animal and human organism.

For example, congenital or acquired genetic defects may result in reduced functionality or an overexpression of proteins. Depending on the function of the respective protein, the organism may be damaged and, thus, diseases may occur. Such genetic defects can be treated by the targeted introduction of nucleic acids into the somatic cells of the patients. Among such nucleic acids are, e.g., all oligomers and polymers of deoxyribonucleic acid (DNA), ribonucleic acid (RNA), siRNA, cyclic DNA (plasmids), antisense oligonucleotides or derivatives of all of these substances. Originally developed for the treatment of monogenetic diseases, the range of applications of a therapy with nucleic acids has meanwhile additionally extended to the fields of cancer, neurological and vascular diseases and infectious diseases.

"Gene silencing" represents an important development step in the treatment of diseases. Here, the expression of the genes which are, among others, responsible for the disease is suppressed by the targeted transport of siRNA into the cells of patients.

Optimization of transport efficiency of nucleic acids into the cells of a patient still represents a huge challenge. During their transport to the site of action, several barriers, such as cell membrane or membranes in the cell interior, have to be passed. In this context, both increasing size and increasing charge state of a molecule represent severe handicaps.

After their application in the animal or human organism, nucleic acids first of all have to find their target cell and, upon contact, have to pass the cell membrane to get into the cell interior. From there, transport into the nucleus or into the cytoplasm takes place next. Nucleic acids are polyanions and, thus, strongly negatively charged molecules which, as a rule, cannot permeate biological membranes, such as the cell membrane. Therefore, nucleic acids have to be transported selectively and effectively into the target cell by means of suitable transport strategies.

In accordance with recent literature, such transport systems have to meet two essential requirements: first of all, they have to compensate for the negative charge of the polyanion and, as has been discussed recently, favourably they have to bring about a conversion into positively charged particles to allow electrostatic interactions with the cell membrane via anionic structures, such as proteoglycans, at the cell surface. On the other hand, the transport systems have to protect the nucleic acid against degradation by, e.g., nucleases.

With transport systems for the group of nucleic acids among the polyanions, a fundamental differentiation is made between "viral" and "non-viral vectors". The skilled person then calls the process of nucleic acid transfer into cells transduction (with viruses) or transfection (without viruses), respectively. As regards other polyanions, at present only non-viral carriers are available. With viral vectors, use is made of the fact that viruses have developed evolutionarily optimized strategies for infiltrating cells with nucleic acids. Although viral vectors are highly efficient, discussions on safety in their application on human patients have increased the search for non-viral alternatives. The problems associated with viral therapy are its immunogenic potential, a possible oncogenic risk as well as generalized viral infections (T. Ratko, J. Cummings, J. Blebea, K. Matuszewski; Clinical gene therapy for nonmalignant disease. Am. J. Med. (2003); 115, 560-569).

Due to these numerous disadvantages, different non-viral alternatives have been developed which basically are also suitable for other polyanions. Among them are cationic, i.e., positively charged substances, such as lipids and polymers. Due to the negative charges, polyanions may interact electrostatically with cations to form small particles. Particles of nucleic acids and cationic lipids are known to the skilled person under the term lipoplexes, particles of nucleic acids and polymers are known to him as polyplexes. The disadvantage of these systems is that their transfection efficiency for the transmission of nucleic acids is lower than with viral systems. That is, considerably less than 100% of the cells respond to the transported nucleic acid to give the desired biological effect.

Like polyplexes and lipoplexes, complexes comprising polycationic compounds as a rule exhibit excess positive charge and, thus, have a number of disadvantages:

1. An interaction with negatively charged cell components may occur which may lead to toxicologically critical effects, such as damage to the cell membrane, inhibition of the metabolic cell activity or even apoptotic or necrotic cell death.
2. Another disadvantage is the difficulty to control the size of these particles. Many of these particles have diameters of more than 100 nanometers. This aggravates their incorporation into the cell and individual cell compartments, such as the nucleus.
3. Excess positive charge which is known to the skilled person in the form of a positive zeta potential results in electrostatic interactions with negatively charged plasma proteins, such as serum albumin, immunoglobulins or fibrinogen. These effects in part result in the adsorption of plasma proteins along with subsequent phagocytosis, in part they result in an aggregation in the blood stream and in part in the adhesion to cells of the blood vessels which may not be identical to the site of action.

There have been attempts to counter these disadvantages of non-viral vectors by means of different, in part combined, strategies. For example, hydrophilic non-ionic polymers, such as polyethylene glycol (PEG), are used as shielding components to reduce unspecific interactions (US20100015050). PEGs prevent the adsorption of proteins, such as those of the plasma, which is accompanied by opsonisation and, thus, increased phagocytosis. Moreover, it is attempted to selectively direct the complexes to their sites of action by attaching specific ligands thereto and simultaneously prevent side-effects (US20040241855). In this context, different types of ligands, such as antibodies, growth factors, vitamins, carbohydrates, integrins or lectins, are used.

Peptides represent an increasingly relevant alternative for complexing polyanions and in particular nucleic acids. Here, a differentiation is made between different types of peptides (A. Mann, G. Thakur, V. Shukla, M. Ganguli; Peptides in DNA delivery: current insights and future directions, Drug Discovery Today (2008), 13, 152-150). On the one hand, there are nucleid acid-compacting peptides, such as linear lysine-based compounds. Due to their large number of positively charged amino acids, they react electrostatically with the nucleic acids to form condensed particles. Moreover, there are cell-penetrating peptides. One differentiates in this context between lysine-rich peptides, such as transportan, and arginin-rich peptides, such as the HIV-1 transactivating transcriptional activator (TAT). Such aggregates are directly incorporated into the cytoplasm of the cells, avoiding the endosomal/lysosomal compartment. Fusogenic peptides represent another group. Their functional principle consists in a change in conformation by lowering the pH in the endosom. This change in conformation allows the interaction with phospholipid membranes and thereby eventually renders the membrane permeable. This group includes natural peptides (e.g., haemaglutinin subunit HA-2 of the influenza virus) as well as synthetic peptides (e.g., GALA, KALA). Endosomolytic peptides are histidin-rich peptides whose principle is based on a protonation of the imidazol group of histidin, which results in the subsequent fusion and destruction of the vesicle membrane. In addition, there are the nucleus localization signal-containing peptides, such as SV40 T-antigen. The latter contain a strongly basic amino acid sequence which typically comprises less than 12 amino acids and is recognized by specific intracellular receptor proteins which allow its transport into the nucleus through pores in the nuclear membrane.

In patent literature (e.g. US2010/0129460 A1), peptides are described which form condensed particles by electrostatic interaction with polyanions and preferably nucleic acids. All in all, however, the use of the above peptides is accompanied by a number of problems:

1. They contain several positive charges which are all capable of reacting with the negative charges of the nucleic acids. Also, the complexes formed in this way have a random, irregular structure and excess positive charge, associated with the problems depicted above.
2. Likewise, due to their charge not only those compounds which are to be introduced into the cells are bonded, but also those which naturally occur in the cell. Consequently, it is often observed that when the above peptides are used for complex formation with polyanions, such as nucleic acids, toxic effects occur, which is prohibitive for use in the animal or human organism.

Moreover, in the field of peptide and protein active agents there is also considerable interest in efficient delivery systems. Successful delivery systems may, for example, positively influence the pharmacokinetics of the active agents, minimize the degradation of the active agent, prevent harmful systemic side-effects, increase biological availability of the active agent and/or allow the reduction of administration frequency. However, with respect to peptides and proteins many of these administration strategies could so far not be implemented in a satisfactory manner since they impose special demands on suitable systems. One approach is to use a hydrogel as a matrix for the active agent to be administered, but often the release profile of the active agent is not at an optimum and rapid release cannot be prevented.

Thus, there is still a need for delivery systems by means of which active agents, such as nucleic acids and their oligomers and polymers, peptides or proteins, may efficiently be administered to the organism and released therein in a preferably controlled manner.

When examining the interactions between polyanions and peptides, it showed that the complexing of anions by specific peptides results in the formation of defined nanostructures. The subject-matter of the invention are complexes of polyanions with peptides exhibiting specific properties. In particular, within the context of the invention, nanocomplexes are provided consisting of a polyanion and cationic amphiphilic peptide molecules in an equimolar ratio to the negative charges of the polyanion. By combining the polyanion with such peptide molecules, complexes are formed which are held together by cooperative molecular interactions. Moreover, a complex material in which these complexes are bonded to a biologically active unit, as well as pharmaceutical compositions containing the nanocomplexes or complex materials are provided.

In the technical field, the term polyanion generally relates to molecules containing several negatively charged groups, e.g. carboxylic acid anions. Within the scope of the invention, preferably those polyanions are used which exhibit a plurality of negatively charged groups at a physiological pH, e.g. at a pH within the range of pH 7.0 to 7.5 in aqueous solutions. In this context, particularly suitable polymers are those containing polymerized subunits comprising one or more anionic groups each. Particularly preferred polyanions according to the present invention are, thus, on the one hand, polysaccharides, such as alginate, hyaluronate, carboxymethyl cellulose, carrageenan or xanthan. Nucleic acids, such as oligomers or polymers of single-stranded or double-stranded ribonucleic acid (RNA) or deoxyribonucleic acid (DNA) may also preferably be used. A polyanion in the sense of the invention may carry more than 10,000 negative charges. Plasmids are an example of such molecules. Alginate, which is another typical polyanion, exhibits about 1,000 negative charges. Small interfering RNA (siRNA) may also be employed as the polyanion, as a single strand and preferably as a double strand, e.g. with 21 charges in the single strand and 42 charges in the double strand, which originate from the phosphate group. Finally, antisense nucleotides can also be mentioned as an example of suitable polyanions. Depending on the pH, the base pairs of DNA and RNA may optionally generate additional positive charges. Derivates of these substances listed by way of example are also suitable in accordance with the present invention, as far as the derivatization does not negatively affect the polyanionic character of the substances.

In the sense of the invention, in particular cationic peptides are used which carry less than 5 positive charges per molecule. Those carrying 2 positive charges are preferred and those carrying 1 positive charge are particularly preferred. Charge carriers may be a corresponding number of natural or non-natural amino acids which carry a positive charge either permanently or depending on the pH. Examples of suitable natural amino acids are arginine or lysine. In terms of the invention, the amino terminal of a peptide alone might also be the charge carrier. In as far as charge occurs as a function of the pH value, peptides carrying less than 5, in particular 2 and particularly preferred 1 positive charge per molecule at a physiological pH, e.g. a pH within the range of pH 7.0 to 7.5 in aqueous solutions, are preferred. Peptides in the sense of the invention may also contain molecular components, which due to their structure are no amino acids, but contain functional groups which may be protonated or are permanently positively charged. In any case, the peptides contain at least one natural or non-natural amino acid. Preferably, cationic peptides for use according to the invention contain up to 20 amino acids. Depending on the need and the desired properties of the complex, the complexes according to the invention may contain one type or a mixture of two or more types of the cationic polymers.

In the complexes according to the invention, the peptides are oriented towards the polyanion in such a manner that they bind to the polyanion via the interaction between positive charge of the peptide with a negative charge of the polyanion. Complexes in terms of the invention are stabilized by the ionic interaction between polyanion and peptide. Additional stabilization is achieved by further molecular interactions between peptide molecules, which results in a cooperative interaction. The cooperative molecular interactions which keep the nanocomplexes according to the present invention together, thus, include both the ionic interactions between polyanion and cationic peptide and also additional cooperative interactions between the cationic peptide molecules. Such interactions may, e.g., be hydrogen bonds or van der Waals' interactions. Further mechanisms are known to the skilled person from the literature relating to molecular interactions or protein/protein interactions. Particularly preferred are peptides of which the individual molecules form hydrophobic interactions among each other. For this purpose, hydrophobic natural or non-natural amino acid or other hydrophobic molecular components are suited. They contain e.g. saturated or unsaturated hydrocarbons or aromatics, such as one or more phenyl groups, one or more naphthyl groups or one or more pyridinyl groups in their molecular structure. In this context, the terms "phenyl" etc. should not be understood in such a way that only monovalent groups of this type can provide a corresponding interaction, but that such aromatics may also be present as divalent or higher valent groups within the peptide. Examples of hydrophobic natural amino acids comprising aromatic rings are tryptophan, tyrosine or phenylalanine.

Cationic peptides which are particularly suitable for the formation of complexes in terms of the invention are amphiphilic. Due to their positive charge for ionic interaction with a negative charge of the polyanion and the hydrophobic structure for interaction with other peptide molecules, such peptides tend to accumulate at interfaces. As a rule, these peptides have one or more of the following abilities: reduction of interfacial tension, lowering surface tension of preferably aqueous liquids, formation of micelles, formation of inverse micelles. Examples of such peptides are known to the skilled person under the names Cetrorelix, Degarelix, Ozarelix or Abarelix.

The complexes of polyanion and peptide are preferably formed spontaneously when two solutions are mixed. For this purpose, polyanion and peptide are mixed together at a defined concentration and defined volume, each dissolved in a solvent, e.g. water. This can be done outside the human or animal organism or in situ, i.e., in the course of application, for example by injection, such as with a dual-chamber syringe. Optionally, it may be necessary to adjust physicochemical parameters, such as pH, ionic strength or osmotic pressure before or after mixing.

It has proven particularly advantageous to adjust the ratio between the polyanions and the cationic peptide molecules in the preparation of the complexes such that an equimolar ratio of the cationic peptide molecules to the negative charges of the polyanion present is achieved in the complex. As pointed out above, it is particularly preferred to use peptides with exactly one positive charge, so that for each Mole of negatively charged groups of the polyanion one Mole of cationic peptide with one charge is present and the charge is equalized in this manner.

The stability of the complexes can be expressed by means of the binding constant K which may, e.g., be determined via isothermal titration calorimetry (ITC).

As a rule, complexes in the sense of the invention have K values which are higher than 10,000 mol$^{-1}$. Complexes having K values higher than 100,000 mol$^{-1}$ are preferred and those having K values above 1,000,000 mol$^{-1}$ are particularly preferred, the corresponding values being easily determinable at room temperature, i.e., 25° C.

Thus, in aqueous solution the positive charge of the peptide can electrostatically interact with the negative charge of a polyanion, such as the phosphate groups of a nucleic acid. By the interaction of further peptide molecules with the polyanion, adjacent molecules are so close to each other that this results in the formation of molecular interactions, such as hydrophobic interactions, between each other. These additional interactions result in a stabilization of the complexes formed. Due to the cooperative electrostatic and, for example, hydrophobic interaction, a "peptide sheath" is formed around the polyanion, which shields the charges of the polyanion against the exterior. In this way, the shape of the complexes may, e.g., be controlled by the selection of the cationic polymers and complexes having a defined shape may be provided the components of which show a regular arrangement.

Figure 1:
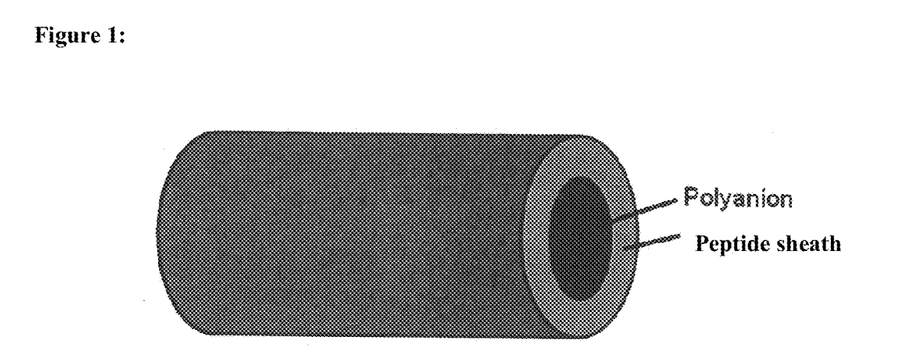
FIG. 1 schematically depicts a complex according to the invention.
Figure 2:
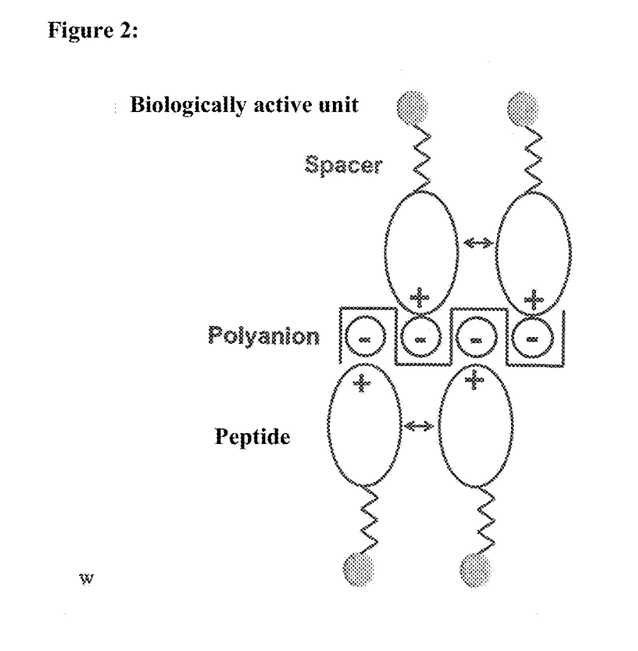
FIG. 2 is a two-dimensional schematic illustration of a complex according to the invention.

An example of such a complex is schematically depicted three-dimensionally in FIG. 1. The skilled person will understand that the side surfaces of the complex depicted as a cylinder represent a section through a typical complex structure. FIG. 2 also illustrates two-dimensionally, by way of example, the structure of a corresponding complex in which single-charge peptides are arranged around a polyanion. If a polyanion having a linear structure is used, according to a preferred embodiment of the invention linear complexes can be produced in this way. The length of the preferably linear complexes is determined by the number of monomers of the polyanion, such as the number of bases of a nucleic acid, and is between 1 and more than 100 nm. The more monomers the chain of a polyanion contains, the "longer" the corresponding complex will be. The diameter of the preferably linear complexes, by contrast, can be controlled via the three-dimensional structure of the amino acid sequence of the peptide. As a rule, the diameter is from 1 to 100 nanometers. Preferably, it is less than 50 nanometers. Diameters of less than 20 nanometers are particularly preferred. Branched polyanions may also result in overall branched complexes.

The ratio of attached peptide molecules per charge-carrying monomer of the polyanion which may, e.g., be determined via isothermal titration calorimetry is between 0.1 and 10. Preferably it is between 0.2 and 5 and particularly preferably between 0.5 and 2. A ratio between 0.9 and 1.1 is to be considered even more preferred, a ratio of 1, in particular, being most preferred.

The complexes may be used as such or may be further modified to form a complex material (cf. FIG. 2). For example, spacers may be linked to the peptides before or after formation of the complex, e.g., by covalent linking by means of reactions known in this technical field. Such spacers may be used as shielding components to protect against enzymes, or, as illustrated above, against the adsorption of proteins and the accompanying opsonisation and subsequent phagocytosis. Depending on its own charge, the spacer may also render the charge of the complex formed neutral or negative. Depending on its purpose, the spacer may have a characteristic chemical structure. The number of spacers may be identical to the number of cationic peptide molecules present in the complex, but it may also exceed the latter (e.g., if more than one spacer is used per peptide molecule) or may be lower. On the one hand, molecules known to the skilled person as so-called linkers are suitable, on the other hand, those selected from the group of polymers can be used. Such polymers may, e.g., have a molar mass of up to 50,000 daltons. Polymers having a molar mass of up to 5,000 daltons are particularly suitable. Those having a molar mass of up to 1,000 daltons are most particularly preferred. Materials which are known to impart stealth properties, such as hydrophilic anionic or non-ionic polymers, are preferably used. Examples are polyethylene glycols, polysaccharides, such as polysialic acid, polyoxyazolines and polyglycerol.

Moreover, the complexes according to the invention may be provided with biologically active units. For example, the transport of the complexes to their target, i.e., for example a specific tissue, a specific cell or an intracellular organelle, may be promoted. In this way, side-effects on healthy or non-target cells may be avoided simultaneously. Such a biologically active unit may be provided by the cationic peptide itself already, i.e. without spacer, if it selectively binds to the target, e.g., via a receptor. Alternatively, a complex material may be formed by modifying the nanocomplexes according to the invention by linking them, preferably covalently, to a biologically active unit. This unit may, e.g., bind directly to the peptide or via a spacer. In this case, the biologically active unit may be linked to the spacer or peptide before or after formation of the complex.

Examples of such biologically active units are ligands for different receptors of the cell surface, antibodies and other molecules known to the skilled person for the purposes of cell or organelle recognition. Depending on the target tissue, both low-molecular weight substances, such as sugar (galactose) or vitamins (folic acid), but also peptides and macromolecules, such as proteins (antibodies) or polysaccharides may be used as ligands. For selective targeting of tumors, receptors of growth factors, such as the epidermal growth factor (EGF), suggest themselves which, due to their metabolic activity or due to mutation, are present in tumor cells in increased numbers at the cell surface. Further target structures for ligands may be G-protein-coupled receptors (GPCR). Likewise, viral receptors are considered to be possible target structures, such as CD4 in the case of HIV, PVR in the case of polio viruses, or sialic acid in the case of influenza viruses. Another example are receptors selected from the group of integrins. Accordingly, complexes in the sense of the invention at least consist of a polyanion and a corresponding number of peptide molecules. The binding of spacers and/or a biologically active unit thereto is optionally possible.

The complexes according to the invention and the modified complex materials are suitable for use in a method for the treatment of the human or animal body by therapy, i.e. mainly for use as a pharmaceutical composition. In this context, the application of the invention in particular includes the use of the complexes for the transfer of drugs, e.g., of nucleic acids, into cells. Complexes having a size of less than 100 nanometers are particularly suitable for the transfer of drugs into tissue, cells and their intracellular compartments and organelles. In this context, drugs are substances which induce a biological effect. Preferably, this can be a pharmacological effect. On the one hand, the polyanion may be the drug, e.g., if it originates from the group of nucleic acids. On the other hand, however, the peptide may also be a drug. Another possibility is that both the polyanion and the peptide are drugs. In this context, interesting combinations of substances are achieved which may act synergistically, for example, in tumor therapy. Here, for example, the siRNA silencing in combination with peptides having cytostatic potential might achieve considerable synergistic effects. Moreover, it is possible to enrich the complexes after intravasal application in the tumor tissue due to the adjustable small size, which is, inter alia, known to the skilled person as "enhanced permeability and retention effect".

The nanocomplexes and complex materials may, however, also be used for the controlled release of drugs after parenteral, in particular non-intravasal, i.e., for example, subcutaneous, intramuscular, intraocular or other local application. In this context, the drug may be effective both locally, i.e., immediately at the site of application, and systemically, i.e., after distribution in the human or animal organism. For example, the complexes in the sense of the invention may be used to control the release of therapeutically active peptides or nucleic acids. Here, complexes having a length of more than 100 nm may be used as well.

The nanocomplexes may be present individually or form larger aggregates. In this context, the aggregate's length may increase without the diameter changing. Moreover, irregular aggregates may also be formed, or even systems having a gel-like character. However, their functionality, in particular for the controlled release of the drug, is maintained.

Therapeutic applications of the nanocomplexes or complex materials, in particular if nucleic acids are used as the polyanion, include, e.g., the therapy of monogenetic diseases, but also of cancer, neurological and vascular diseases as well as infectious diseases.

Pharmaceutical agents which are provided within the scope of the invention may consist of the nanocomplexes or complex materials as such, or may contain the nanocomplexes or complex materials together with adjuvants known in the technical field, for example, selected from diluents including solvents, substances for adjusting desired salt concentrations and/or a desired pH value and preserving agents. Suitable pharmaceutically acceptable adjuvants which may be used in the preparation of the pharmaceutical compositions according to the present invention are known to the skilled person and are, for example, described in Remington's Pharmaceutical Sciences, 15$^{th}$ ed., Mack Publishing Co., New Jersey (1991).

Suitable pharmaceutical dosage forms can be provided by pharmaceutical technical production methods which are well-established in this technical field. In this context, a large number of the dosage forms known to the skilled person may be suitable for the formulation of the nanocomplexes and complex materials. Examples of pharmaceutical dosage forms are solid dosage forms (e.g., lyophilisates, powders, granules, tablets, pills, capsules, implants etc.), semi-solid dosage forms (e.g., ointments, gels, wound dressings, emulsions, suspensions etc.), liquid dosage forms (solutions, injection and infusion preparations, ocularia etc.) and therapeutic systems (e.g. oral osmotic therapeutic systems, transdermal systems, inserts etc.). By way of example, reference shall be made here to Pharmaceutical Dosage Forms and Drug Delivery Systems, H. C. Ansel et al., eds., 7$^{th}$ ed., Lippincott, Williams, & Wilkins (1999).

Depending on the individual nanocomplex or complex material used and the dosage form selected, administration may be achieved in numerous ways known to the skilled person. Examples thereof are peroral, inhalative, topical, intravenous, intraperitoneal, subcutaneous and intramuscular administration.

Preferably, the nanocomplexes and complex materials are formulated as solutions or suspensions suitable for parenteral application. In this context, a pharmaceutical composition according to the invention may be formulated advantageously by mixing polyanions with polycations, optionally with the addition of further adjuvants. As an equally preferred embodiment, it is to be considered that the dosage forms suitable for parenteral application are lyophilized in advance. Lyophilization may be useful above all to guarantee sufficient storage stability of the dosage form to be administered. Suitable lyophilisation methods as well as conventionally used additives (e.g., cryoprotective additives, such as lactose, mannitol, etc.) are known to the skilled person. In the case of lyophilisation, e.g., a solution to be administered may be prepared shortly/immediately before use by uptake of the lyophilisate in suitable solvents, such as water for injection, isotonic saline solution, Ringer's solution etc.

It may also be considered to prepare the nanocomplexes or complex materials according to the invention immediately before or during application by mixing the components or even to have them prepared within the body, e.g. after parallel administration or administration of the components within short time intervals.

EXAMPLES

Example 1

Somatostatin is dissolved in water, pH=6, at a concentration of 0.225 mg/ml. Double-stranded RNA (strand 1, SEQ ID NO 1: r(GCAAGCUGACCCUGAAGUUCA)dT, strand 2, SEQ ID NO 2: r(GAACUUCAGGGUCAGCUUGCC)dT) consisting of 22 base pairs is also dissolved in water at a concentration of 0.04 mg/ml. In this context, the respective amounts are calculated such that a charge equalization between positive and negative charge is achieved. For this purpose, the concentration of the nucleic acid solution is divided by the molar mass of the double-stranded RNA and by 2 (positive charges per somatostatin molecule) and subsequently multiplied by 44 (amount of negative charges per mol of RNA) and the molar mass of the somatostatin to obtain the concentration of the somatostatin solution. 1 ml of the nucleic acid solution is supplied in an Eppendorf tube and 1 ml of the peptide solution is slowly dripped in. Subsequently, the solution is thoroughly mixed on a vortex mixer at room temperature. Subsequently, the solution is placed on a laboratory shaker for 1 h at room temperature to ensure the formation of an equilibrium between the complex and the free components.

Figure 3:
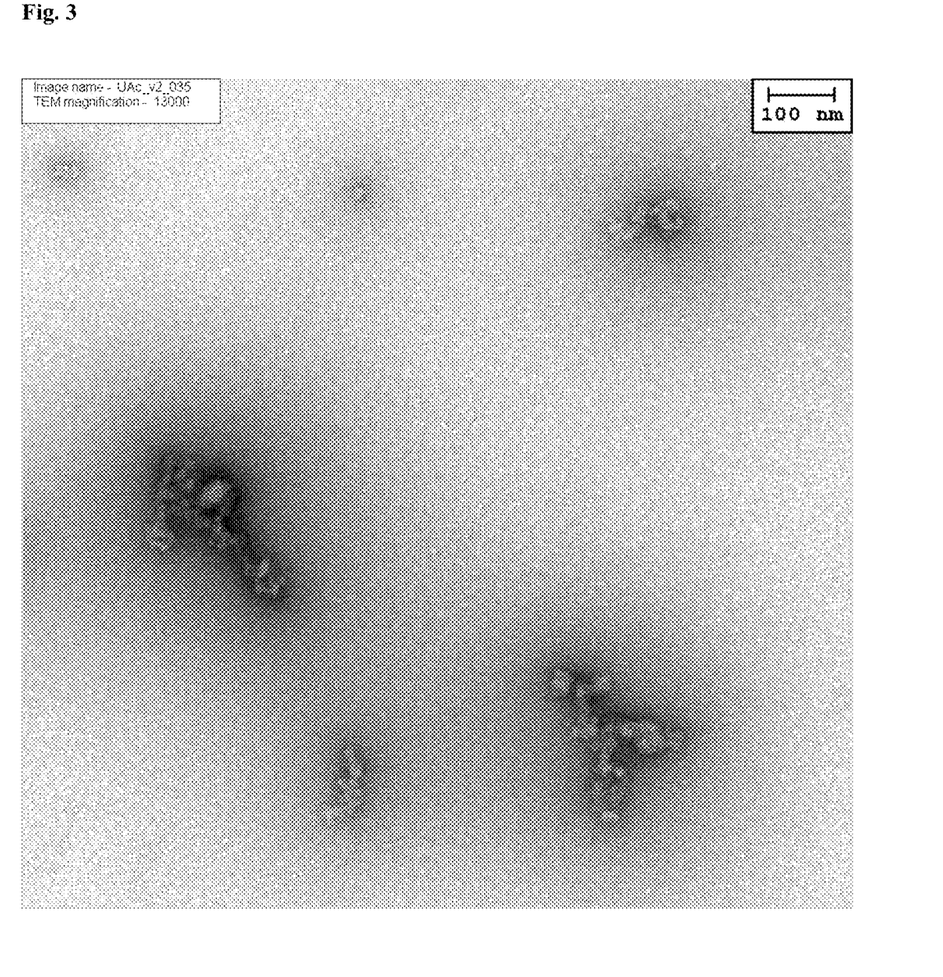
FIG. 3 shows a transmission electron micrograph of the nanocomplexes formed of somatostatin and double-stranded RNA of Example 1.

FIG. 3 shows a transmission electron micrograph of the nanocomplexes formed of somatostatin and double-stranded RNA of Example 1.

Example 2

The starting solutions are prepared by analogy with Example 1. However, now the peptide solution is first supplied and subsequently the nucleic acid solution is slowly dripped in. Subsequently, the solution is again thoroughly mixed.

Example 3

Figure 4:
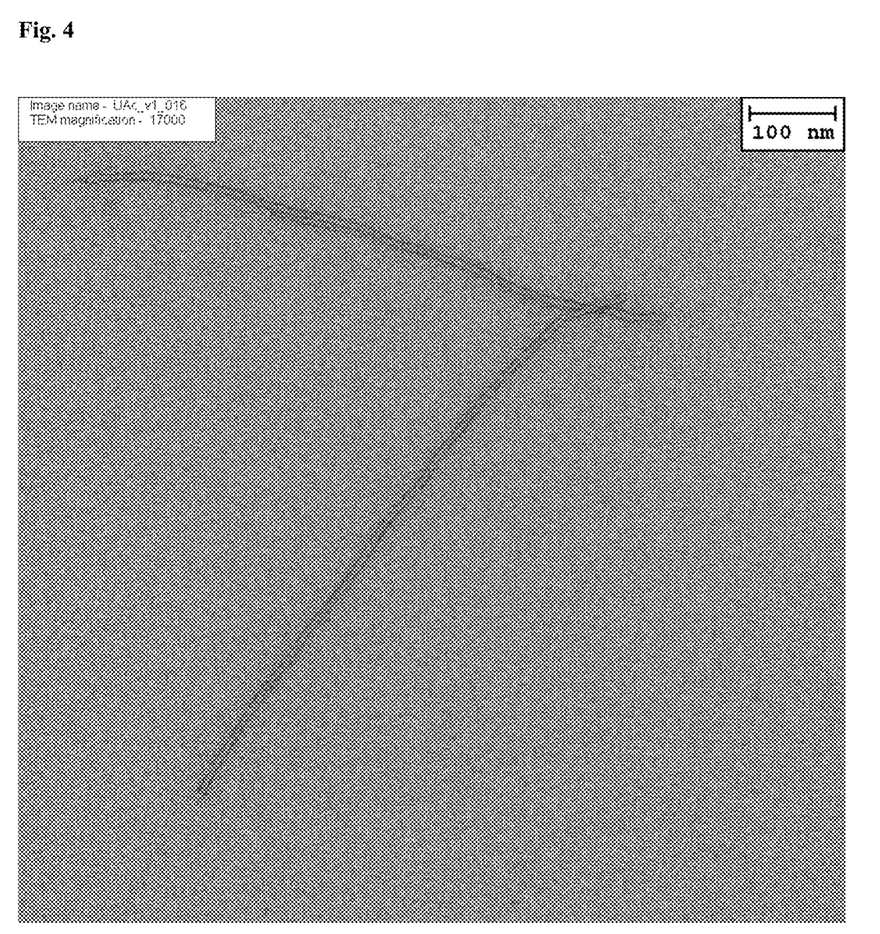
FIG. 4 shows the transmission electron micrograph of nanocomplexes formed of Ozarelix and double-stranded RNA of Example 3.

In a similar manner as in Example 1, apart from the fact that as the cationic polymer Ozarelix is used in a corresponding amount, taking one positive charge per peptide molecule into account, nanocomplexes are prepared by the use of the double-stranded RNA. FIG. 4 shows the transmission electron micrograph of nanocomplexes formed of Ozarelix and double-stranded RNA.

Example 4

Cetrorelix is dissolved in water at a concentration of 0.00175 mmol/l. Double-stranded DNA (strand 1, SEQ ID NO 3: ATGAACTTCAGGGTCAG TTGC, strand 2, SEQ ID NO 4: TACTTGAAGTCCCAGTCGAACG) consisting of 22 base pairs at a concentration of 0.0019 mmol/l is dissolved in a buffer consisting of 10 mmol/l of tris, 100 mmol/l of NaCl and 1 mmol/l of EDTA. Both solutions were degasified immediately before measurement with gentle stirring. 1.435 ml of double-stranded DNA are supplied in the reaction cell of the ITC and slowly titrated with 0.3 ml of the Cetrorelix solution. Here, 10 µl of the Cetrorelix solution are dripped in each over 10 seconds and subsequently an interval of 180 seconds is observed before the next droplet is added to record the total amount of heat released. The experiment is carried out at 25±1° C.

Figure 5:
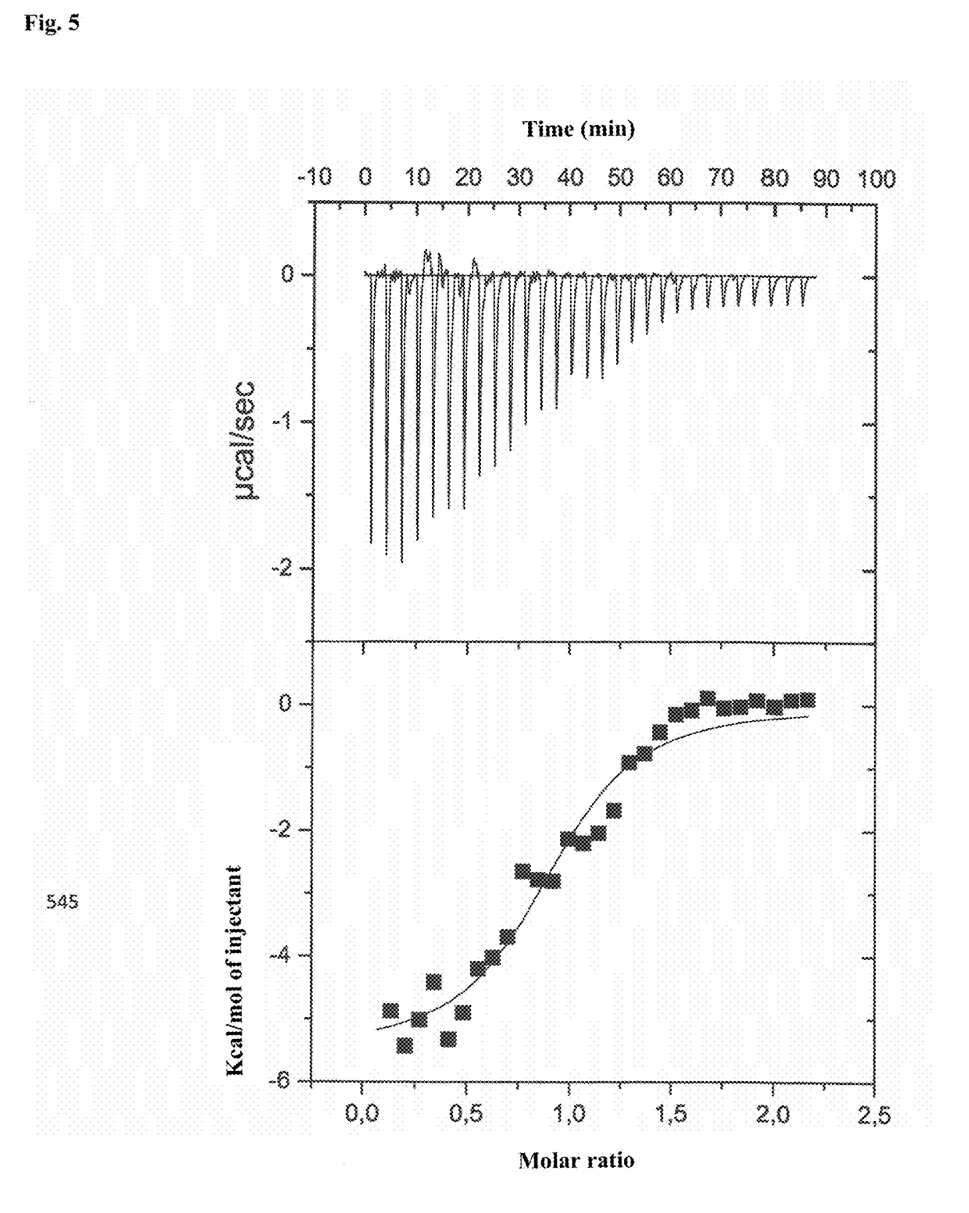
FIG. 5 shows the thermogram of the binding of DNA and Cetrorelix of Example 5 determined by means of ITC.

The data are evaluated using MicroCal Origin 5.0 (MicroCal) software. For this purpose, a non-linear fit is used. By the use of the "one-set of binding sites" model, the thermodynamic constants of standard reaction enthalpy ($\Delta H$), binding constant (K), standard reaction entropy ($\Delta S$) and the stoichiometric ratio of the reaction (n) can be calculated. The resulting complex exhibits a high binding constant in the range of $10^5$, which is indicative of strong binding with electrostatic and hydrophobic interactions. The negative value for $\Delta H$ and the positive value for $\Delta S$ are favourable from an energetic point of view, respectively, $\Delta S$ representing the hydrophobic interactions and $\Delta H$ being indicative of the electrostatic interactions and hydrogen bonds. The stoichiometric ratio of 0.9247 shows that one positively charged peptide each binds to a negative charge of the double-stranded DNA. The following table shows the thermodynamic parameters of the DNA Cetrorelix complex. FIG. 5 shows the thermogram of the binding of DNA and Cetrorelix determined by means of ITC.

TABLE 1

Thermodynamic parameters of the DNA Cetrorelix complex

| | |
|---|---|
| n | 0.9247 (±0.0330) |
| K (M$^{-1}$) | 2.312 × 10$^5$ (±6.696 × 104) |
| $\Delta H$ (cal * mol$^{-1}$) | −5515 (±277.9) |
| $\Delta S$ (cal * mol$^{-1}$ * K$^{-1}$) | 6.044 |

The invention claimed is:

1. Geometrically defined nanocomplexes consisting of a polyanion and cationic amphiphilic peptide molecules which carry one positive charge each and which contain up to 20 amino acids each at an equimolar ratio to the negative charges present, wherein the nanocomplexes are kept together by cooperative molecular interactions and in that the nanocomplexes have a linear form and a diameter of less than 20 nm.

2. The nanocomplexes according to claim 1, wherein the polyanion, the peptide molecules or both are a drug for application in an animal or human organism.

3. The nanocomplexes according to claim 1, wherein the polyanion is selected from the group consisting of polysaccharides and nucleic acids.

4. A complex material in which the nanocomplexes according to claim 1 are linked to a biologically active unit for the selective recognition of tissues, cells or organelles.

5. The complex material according to claim 4, wherein the biologically active unit is linked to the nanocomplex via a spacer.

6. A method for formulating a pharmaceutical composition which method comprises mixing polyanions with peptide molecules to form the nanocomplexes according to claim 1.

* * * * *